United States Patent [19]
Connell et al.

[11] 3,940,428
[45] Feb. 24, 1976

[54] METHANOL PRODUCTION

[75] Inventors: Anthony John Connell; Alwyn Pinto, both of Stockton-on-Tees, England

[73] Assignee: Imperial Chemical Industries Limited, London, England

[22] Filed: Dec. 7, 1972

[21] Appl. No.: 313,164

Related U.S. Application Data

[63] Continuation of Ser. No. 883,126, Dec. 8, 1969, abandoned.

[30] Foreign Application Priority Data

Dec. 30, 1968  United Kingdom............... 61663/68

[52] U.S. Cl. ............................................. 260/449.5
[51] Int. Cl.² ........................................... C07C 31/04
[58] Field of Search.................................. 260/449.5

[56] References Cited
UNITED STATES PATENTS

| | | | |
|---|---|---|---|
| 2,198,553 | 4/1940 | Roberts et al. ...................... | 252/373 |
| 2,281,228 | 4/1942 | Brown................................ | 260/449.5 |
| 2,904,575 | 9/1959 | Peet.................................... | 260/449.5 |
| 3,064,029 | 11/1962 | White................................. | 260/449.5 |
| 3,337,291 | 8/1967 | Clay.................................... | 23/2 |
| 3,382,045 | 5/1968 | Habermehl et al. ................. | 423/655 |
| 3,501,516 | 3/1970 | Parrish............................... | 260/449.5 |
| 3,531,266 | 9/1970 | Chernoff............................. | 260/449.5 |
| 3,598,527 | 8/1971 | Quartulli et al.................. | 260/449.5 |
| 3,615,200 | 10/1971 | Konaki et al. .................... | 260/449.5 |

FOREIGN PATENTS OR APPLICATIONS

| | | | |
|---|---|---|---|
| 1,010,871 | 11/1965 | United Kingdom.............. | 260/449.5 |
| 1,489,682 | 6/1967 | France.............................. | 260/449.5 |
| 1,104,628 | 2/1968 | United Kingdom................ | 212/376 |

*Primary Examiner*—Howard T. Mars
*Attorney, Agent, or Firm*—Cushman, Darby & Cushman

[57] ABSTRACT

In a process for producing methanol from a gaseous hydrocarbon feedstock, such as natural gas, containing more than the stoichiometric ratio of hydrogen to carbon, the hydrocarbon is subjected to steam reforming to give synthesis gas, the synthesis gas is incompletely reacted over a catalyst to give methanol, methanol is removed from the gas, the unreacted gas is treated to remove carbon monoxide or carbon dioxide from it, and the carbon monoxide or carbon dioxide or both is recycled to the methanol synthesis. By this means the concentration of carbon monoxide or carbon dioxide or both in the gas passing over the synthesis catalyst is kept at a higher level, thus increasing the efficiency of the synthesis and wastage of feedstock is avoided. At the same time a useful high-purity by-product hydrogen stream is produced.

7 Claims, 1 Drawing Figure

U.S. Patent   Feb. 24, 1976   3,940,428
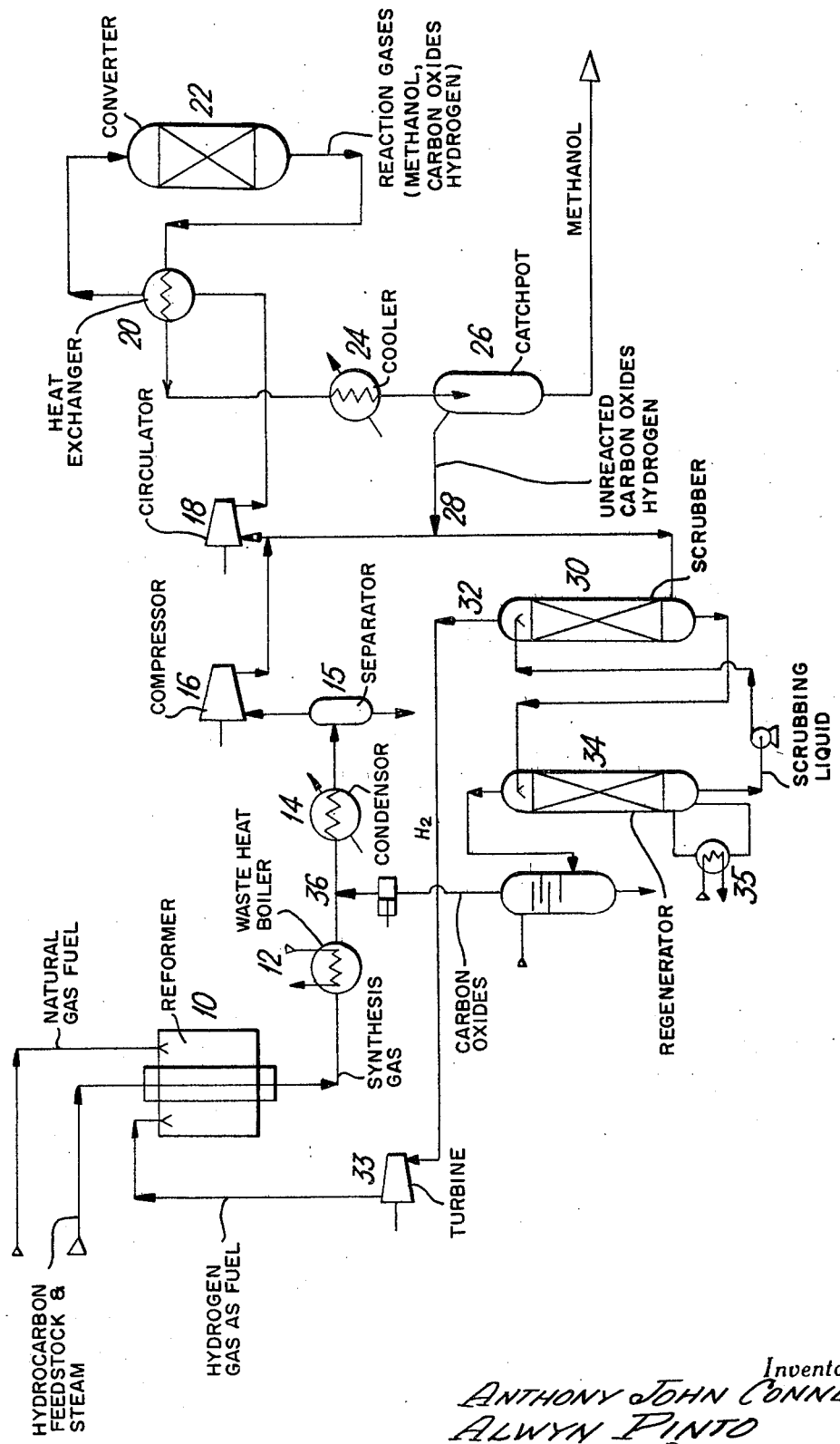
Inventors
ANTHONY JOHN CONNELL
ALWYN PINTO
By
Cushman, Darby & Cushman
Attorneys

METHANOL PRODUCTION

This is a continuation of application Ser. No. 883,126, filed Dec. 8, 1969 and now abandoned.

This invention relates to a process for producing methanol from a hydrocarbon feedstock containing more than two hydrogen atoms per carbon atom.

In order to produce methanol from such a hydrocarbon feedstock it is first necessary to convert the feedstock to a mixture of carbon oxides and hydrogen. The most convenient process of doing this is to react the hydrocarbon with steam over a catalyst in the so-called steam reforming process, then to cool the resulting gas and condense out the steam. When the hydrocarbon feedstock is normally liquid, for example having a boiling range of about 30°–220°C, this process is very convenient as the starting point for methanol manufacture, since the empirical formula of the hydrocarbon is about $CH_2$, so that the hydrocarbon when reacted with steam gives a synthesis gas having a hydrogen to carbon ratio which is about stoichiometrically correct for synthesising methanol.

When however a saturated gaseous hydrocarbon feedstock is used, for example methane, use of the steam reforming process gives rise to the problem that the synthesis gas contains too much hydrogen. Obviously the synthesis gas, after as great a proportion of it as is practicable has been reacted to give methanol, can be used in various ways, such as for ammonia manufacture, for hydrogenations and petroleum treatments or as a fuel. Alternatively carbon oxides can be introduced from other sources, for example carbon dioxide from flue gases, or a partial oxidation process can be used instead of steam-reforming. Either of these involves higher capital and running costs. Our invention provides a process in which the proportion of synthesis gas reacted is increased substantially, and which affords a significant over-all decreases in cost per ton of methanol output, despite the use of some extra plant items.

According to the invention a methanol synthesis process is fed with a synthesis gas derived from steam reforming a gaseous hydrocarbon feedstock containing more than the stoichiometric ratio of hydrogen to carbon oxides, the gas is incompletely reacted to give methanol, methanol is removed from the gas, the remaining gas is treated to remove carbon monoxide or carbon dioxide or both from it, and the carbon monoxide or carbon dioxide or both is recycled to the methanol synthesis.

The synthesis gas is preferably made by steam reforming a hydrocarbon feedstock having an empirical formula $CH_x$ where $x$ is between 2 and 4. Very suitably $x$ is 4, as in methane. In important forms of the invention $x$ is between 2.5 and 4, for example when the feedstock is butane, propane or ethane or mixtures of these gases.

The process of the invention is equally advantageous when the hydrocarbon feedstock is a hydrogen-containing hydrocarbon gas mixture, such as petroleum refinery waste gas. This could for example be a mixture of methane and hydrogen, in which $x$ would be greater than 4, or a mixture of unsaturated or saturated gaseous hydrocarbons with hydrogen.

The extent to which the synthesis gas is reacted to give methanol is usually a matter of choice on economic grounds, since although in principle it is possible to increase the extent of reaction up to the equilibrium limit by increasing the volume of catalyst, too much extra capital cost due to the necessary large catalytic converter and large catalyst volume cannot always be justified. Furthermore, the equilibrium which can be reached at industrially convenient pressures over even the best catalysts leaves a considerable concentration of carbon monoxide or carbon dioxide or both in the synthesis gas. The use of residual synthesis gas in the ways mentioned thus results in waste of part of the carbon content of the feedstock and excessive cost in reforming it.

The process of the invention is preferably a circulatory process, that is, one in which the synthesis gas is only partly converted to methanol in each passage over the catalyst, the unreacted gas being recycled to the synthesis catalyst after removal of methanol from it. In this type of process the hydrogen content of the gas passing over the catalyst builds up to a high value, and the content of carbon oxides steadily falls, as the product methanol is removed from the system. When the hydrogen content reaches a predetermined design level it is necessary to purge off part of the circulating gas. Without the modification provided by the invention it would typically be desirable to purge when the hydrogen content reached 75–85% and the total carbon oxides fall to 6–10%, in order to obtain an economic compromise between the expense due to wasted carbon oxides and the expense of circulating the excess hydrogen. Using our invention the total carbon oxides content of the purge gas can economically be 10–15%, since they are not lost or only partly lost. Since all the carbon oxide is eventually converted to methanol, correspondingly less hydrogen is purged than in the usual process.

If the fed synthesis gas contains inert gases, such as hydrocarbons, nitrogen or noble gases, these are (with the hydrogen) separated from the purge gas by the treatment to recover carbon monoxide or carbon dioxide or both. Consequently by the process of the invention an excessive build-up of such inert gases in the circulating gas is avoided and higher conversions to methanol made possible.

The removal of carbon oxides can be effected in any suitable way. The most convenient method is to scrub the unreacted gas with a cuprammonium solution, since such a solution absorbs both carbon monoxide and carbon dioxide and readily liberates both when the pressure is let down or the temperature is increased or both.

If it is desired only to recover carbon dioxide from the unreacted gas, it is sufficient to scrub the gas with an alkali carbonate or amine solution or other carbon dioxide solvent according to known methods, many variants of which have been devised.

In a further modification the unreacted gas is subjected to shift reaction with steam. Preferably a low-temperature shift process is used so that the carbon monoxide level can be readily reduced to less than 1%. Thereafter the carbon dioxide formed in the shift stage, together with any carbon dioxide already present, is recovered as described in the previous paragraph.

The hydrogen stream recovered from the purge gas can be used in hydrodesulphurising the hydrocarbon feed to the methanol production process, using, for example, a cobalt-molybdenum catalyst followed by a zinc oxide bed. This hydrogen stream is especially valuable for this purpose if it has been recovered by use of a cuprammonium solution or by a combination of shift and carbon dioxide removal and contains less than 2% of carbon monoxide.

A further method which can be used to assist the recovery of carbon dioxide comprises the combination with the methanol synthesis process of a shift stage upstream of the synthesis. By this means the fresh synthesis gas contains more carbon dioxide in proportion to carbon monoxide than it otherwise would, and the purge gas also contains more carbon dioxide. Consequently a substantial recovery of carbon as carbon dioxide is achieved, although some carbon monoxide is lost.

It will be appreciated that the preferred methanol synthesis according to the invention includes two recycle loops, one being the recycle of synthesis gas to the catalyst after removal of methanol, the other being the recycle of the carbon oxides of the purge gas to the synthesis. If the hydrocarbon feedstock contains only a small excess of hydrogen, for example is of a formula about $CH_{2.5}$ to $CH_{3.5}$, and especially if the methane content of the fresh synthesis gas is relatively high, for example 2–10%, it may be desirable to return part of the methane and hydrogen, after removal of carbon oxides, to the synthesis gas generation stage; then the total plant contains three recycle loops.

If the process includes two or more synthesis loops in series, the carbon oxides can be returned to either loop.

The invention can be applied to methanol synthesis processes at any pressures, including both the so-called "high-pressure" and "low pressure" processes. The synthesis is preferably at a pressure below 150 atmospheres, for example 10–150 and especially 30–120, for example 40–80 atmospheres. The temperature is preferably in the range 160°–300°C especially 190°–270°C. Such processes can be conveniently operated using copper-based catalysts, especially those containing copper, zinc oxide and a metal oxide component selected from chromium and metals from Groups II to IV of the Periodic Table, especially aluminium or magnesium, as described, respectively in U.S. Pat. No. 3,326,956 and in U.K. Pat. No. 1,159,035 corresponding to U.S. application Ser. No. 570,687 filed Aug. 8th 1966.

The proportion of carbon dioxide in the synthesis gas should be at least sufficient to afford the higher conversion which is characteristic of the copper-catalysed methanol synthesis using carbon dioxide-containing gas as compared with such a synthesis in which substantially the only carbon oxide is the monoxide. If it is not objectionable to produce a crude methanol containing a substantial proportion of water, for example up to 36% w/w apart from any water added in a scrubber, the synthesis gas can contain carbon dioxide but substantially no carbon monoxide. Usually however the percentage by volume of carbon dioxide in the synthesis gas is 1–20, especially 3–12, and is preferably between half and double the carbon monoxide content.

The accompanying flow diagram shows schematically two methanol synthesis processes according to the invention. The synthesis gas is generated by reacting natural gas with steam over a nickel catalyst in externally heated tubular reformer 10 whence it flows, via waste-heat boiler 12 and condenser 14 and separator 15 in which steam is substantially removed from it, to the inlet of centrifugal compressor 16 which raises its pressure from the generation pressure of 21.5 atmospheres to the synthesis pressure 50 atmospheres. It then passes through circulator 18 and feed/product heat exchanger 20 to synthesis converter 22. The gas leaving the converter, now containing methanol vapour, passes through the product side of heat exchanger 20, where it gives up its heat to incoming gas, to cooler 24 where methanol is condensed out, and catchpot 26 where methanol is separated. The unreacted gas passes partly back to circulator 18 and repeats its passage through the converter. The remainder of the unreacted gas, that is, the "purge gas", is diverted at 28 and passes into the scrubber 30 in which one or both carbon oxides is removed, as described specifically in relation to processes (B) and (C) of the Example. Hydrogen and inert gases pass out at 32 and are fed via power recovery turbine 33 as fuel to the reformer furnace 10, part of the fuel supply being natural gas. The scrubber liquor is let down in pressure in regenerator 34, the gas evolved being washed, compressed and fed into the fresh synthesis gas line at 36 and the liquor being returned to the scrubber. The process is self-sufficient in steam as a result of heat recoveries from the reformer gas in waste-heat boiler 12 and in a reformer flue-gas waste-heat boiler (not shown), the steam being used in turbines to drive the compressor 16, circulator 18 and other machines, in regenerator reboiler 35 and in the final methanol distillation (not shown).

EXAMPLE

A methanol process producing 935 tonnes per day of methanol is fed by a steam/natural gas endothermic tubular reformer operated at an exit pressure of 21.5 atmospheres, exit temperature 825°C and steam ratio 4.0. The fresh synthesis gas so produced is fed to a methanol synthesis system operated at a catalyst outlet temperature of 270°C, pressure 48 atm. absolute, with a flow pattern as described above, two methods of carbon oxide recycle being employed, one (B) involving hot potash scrubbing, the other (C) cuprammonium solution scrubbing. In comparison with process A, in which all the purge gas is burnt as fuel, the Table shows the compositions and flow rates of fresh synthesis gas and purge gas, together with the flow rates of recovered and recycled carbon oxides and the relative radiant heat loads and natural gas consumption rates of the primary reformer required to maintain the same methanol output by the three processes.

(It will be appreciated that Process A does not employ items 30, 34 and 3b and is not according to the invention).

TABLE

|  |  | A | B | C |
|---|---|---|---|---|
| Fresh synthesis gas | CO | 11.0 | 10.8 | 12.4 |
|  | $CO_2$ | 10.5 | 12.0 | 11.7 |
|  | $H_2$ | 73.1 | 71.9 | 70.6 |
|  | $CH_4$ | 4.8 | 4.7 | 4.6 |
|  | $N_2$ | 0.6 | 0.6 | 0.6 |
| Flow rate $\overline{R}M^3/hr$ |  | 168237 | 156942 | 144740 |
| Purge gas | CO | 5.1 | 5.7 | 6.1 |
|  | $CO_2$ | 4.4 | 5.7 | 5.8 |
|  | $H_2$ | 75.8 | 72.1 | 69.2 |
|  | $CH_4$ | 12.5 | 14.2 | 16.2 |
|  | $N_2$ | 1.6 | 1.8 | 2.1 |
|  | $CH_3OH$ | 0.5 | 0.5 | 0.5 |
| Flow rate $\overline{R}M^3/hr$ |  | 64038 | 51433 | 40714 |
| Recycled ($\overline{R}M^3/hr$) | $CO_2$ | — | 2789 | 2359 |
|  | CO | — | — | 2474 |
| Reformer radiant heat load (tonnecal./hr.) |  | 104494 | 95605 | 86768 |
| relative to A |  | 100 | 91.4 | 83.0 |
| Natural gas consumption (million B.Th.U. (NOV) |  |  |  |  |

TABLE-continued

|  | A | B | C |
|---|---|---|---|
| per tonne of CH$_3$OH | | | |
| as feedstock | 36.4 | 33.3 | 30.3 |
| as fuel | 0.6 | 2.6 | 4.8 |
| total | 37.0 | 35.9 | 35.1 |

It is evident that a substantial and economically significant decrease in the radiant heat load of the primary reformer has been effected, especially by process C. Further the natural gas consumption is substantially decreased. This is especially significant for manufacturers whose supplies of natural gas need desulphurisation, since the decreased consumption of feedstock (i.e. purified) gas is especially marked.

If desired the advantage of the use of the invention could be equally well obtained by keeping the primary reformer capacity at its level as in process A and increasing the output of methanol.

We claim:

1. In a process for producing methanol from a gaseous aliphatic hydrocarbon feedstock of empirical formula CH$_x$ where x is between 2 and 4 which comprises steam reforming the feedstock to give a synthesis gas containing hydrogen and at least one carbon oxide selected from the group consisting of carbon monoxide and carbon dioxide, the amount of hydrogen in the resulting synthesis gas being in excess of the stoichiometric amount necessary to form methanol, and reacting the synthesis gas in a catalytic synthesis stage using a copper catalyst to obtain methanol, the improvement which comprises reacting the synthesis gas incompletely in said catalytic synthesis stage to give a reaction product of methanol and unreacted hydrogen and carbon oxide, separating methanol from the remaining gas in said reaction product, recycling the remaining gas comprising unreacted hydrogen and carbon oxide to said synthesis stage for further reaction to form more methanol, and controlling the amount of hydrogen thereby recycled to said synthesis stage to prevent undesired build-up of hydrogen in said synthesis stage by withdrawing a part of said remaining gas before it is recycled to said synthesis stage, separating the carbon oxide from the hydrogen in this withdrawn part and recycling only the separated carbon oxide from said withdrawn part to said synthesis stage for reaction with hydrogen to form further methanol.

2. A process according to claim 1 in which the total carbon oxides content of the remaining gas is in the range 10-15%.

3. A process according to claim 1 in which carbon monoxide and carbon dioxide are removed from the remaining gas by scrubbing with a cuprammonium solution.

4. A process according to claim 1 in which the remaining gas is subjected to shift reaction with steam to convert any carbon monoxide therein to carbon dioxide before separating carbon dioxide from it.

5. A process according to claim 1 in which there is used a shift stage upstream of the synthesis stage.

6. A process according to claim 1 in which methanol synthesis is effected by a copper-based catalyst containing copper, zinc oxide and a metal oxide component selected from chromium and metals from Groups II to IV of the Periodic Table.

7. A process according to claim 6 in which the synthesis pressure is below 150 atmospheres.

* * * * *